United States Patent [19]

Ansell et al.

[11] Patent Number: 5,087,686
[45] Date of Patent: Feb. 11, 1992

[54] CURABLE COMPOSITIONS

[75] Inventors: Christopher W. G. Ansell, Cambridge; Colin Butler, Upper Boddington, both of United Kingdom

[73] Assignee: Smith and Nephew p.l.c., United Kingdom

[21] Appl. No.: 237,783

[22] Filed: Aug. 29, 1988

Related U.S. Application Data

[63] Continuation-in-part of Ser. No. 129,526, Dec. 7, 1987, abandoned.

[30] Foreign Application Priority Data

Aug. 28, 1987 [GB] United Kingdom ............... 8720440

[51] Int. Cl.$^5$ ............................................. C08G 18/14
[52] U.S. Cl. ................................. 528/49; 428/423.1
[58] Field of Search ....................... 528/49; 428/423.1

[56] References Cited

U.S. PATENT DOCUMENTS

| | | | |
|---|---|---|---|
| 3,782,961 | 1/1974 | Takahashi et al. | 96/115 |
| 4,119,681 | 10/1978 | Veselovsky | 250/859 |
| 4,133,723 | 1/1979 | Howard . | |
| 4,192,762 | 3/1980 | Osborn | 252/182 |
| 4,465,718 | 8/1984 | Gruber | 528/49 |
| 4,672,001 | 6/1987 | Bravet et al. | 428/442 |

FOREIGN PATENT DOCUMENTS

| | | |
|---|---|---|
| 0094222 | 11/1983 | European Pat. Off. . |
| 1441108 | 6/1976 | United Kingdom . |
| 2198949 | 6/1988 | United Kingdom . |
| 2199040 | 6/1988 | United Kingdom . |

OTHER PUBLICATIONS

*Encyclopedia of Polymer Science and Engineering*, vol. 1, pp. 548–551 (1985), John Wiley & Sons.
*Handbook of Adhesives*, Third Edition, Van Nostrand Reinhold, pp. 5–8 (1990).

*Primary Examiner*—Maurice J. Welsh
*Attorney, Agent, or Firm*—Rosenman & Colin

[57] ABSTRACT

A radiation curable composition for an adhesive includes a polyurethane, for example a polyurethane comprising residues of a polyether diol or a polyester diol, capped with residues of a hydroxyalkyl acrylate or methacrylate and non-polymerizable residues of a primary or secondary alcohol. The compositions may be cured to form a pressure sensitive adhesive and can be employed to produce adhesive dressings by coating a suitable substrate with the composition and thereafter curing the coated composition by, for example, electron beam or ultra violet irradiation.

27 Claims, No Drawings

CURABLE COMPOSITIONS

This is a continuation-in-part of U.S. Ser. No. 129,526, filed Dec. 7, 1987, and now abandoned, entitled Adhesives, their Preparation and Use, and which application is incorporated herein by reference.

The invention relates to curable compositions, cured pressure sensitive adhesives formed therefrom and adhesive products comprising these adhesives. More particularly, the invention relates to compositions which are radiation cured to form adhesives and adhesive products.

Adhesive products such as adhesive surgical or medical dressings normally comprise a layer of a pressure sensitive adhesive. Such a layer of adhesive is commonly provided by coating a solution of the adhesive in volatile organic solvent onto a suitable substrate and drying the coating in a heated oven. Solution coating of adhesives, however, can be hazardous due to the flammability or toxicity of the solvents such as toluene commonly used in adhesive solutions. Furthermore, an adhesive solution coating process in which the solvent is not recovered or in which the coated adhesive layer is a relatively thick layer and requires a long drying time may be relatively uneconomic. A solventless coating process of providing an adhesive layer would therefore be an advantage. It is known that liquid oligomer compositions containing unsaturated end groups can be coated on a substrate and cured rapidly by radiation such as electron beam or ultra violet light radiation to form adhesive layers. U.S. Pat. No. 4,022,926, discloses a method of making adhesive labels in which the adhesive and base layers are formed by radiation curing. The patent further discloses that curable compositions for both layers preferably comprise a polyurethane capped with residues of a hydroxy alkyl acrylate or methacrylate. This patent teaches, however, that the curable composition for the adhesive layer is prepared by adding tackifying resins or agents to the curable composition used for the base layer.

In our Patent Application No. GB 2199040A, cross-linked adhesives are disclosed, cured by ultra violet radiation, which are formed by reaction of an isocyanate prepolymer with an hydroxyl-containing ester of acrylic or methacrylic acid and another hydroxyl-containing compound. The prepolymer is the reaction product of a polyfunctional isocyanate and a polyoxyalkylene diol mono alkyl ether. Since the oxyalkylene residues are derived from monofunctional alcohols, they will form pendant groups off a main polymer chain or backbone.

Radiation curable compositions for adhesives have now been found which comprise a polyurethane capped with residues of hydroxyalkylacrylate or methacrylate which do not require the addition of tackifying agents or resins to render the cured composition adhesive.

Accordingly the present invention provides a radiation curable composition for an adhesive including a polyurethane capped with residues of a hydroxyalkyl acrylate or methacrylate and non-polymerisable residues of a primary or secondary alcohol. The polyurethane may comprise residues of a polyether or polyester diol.

Non-polymerisable residues as used herein are residues which do not polymerise with isocyanate or unsaturated groups.

The alcohol residues will normally be mono alcohol residues, preferably derived from a primary mono alcohol.

It has been found that the pressure of the alcohol residues renders the composition of the invention pressure sensitive adhesive when it is radiation or, indeed, thermally cured without the need to add tackifying resins or agents. Adhesives formed from the compositions of the invention are thus 'internally' tackified.

The alcohol residues may contain unsaturated groups which do not polymerise or copolymerise with the acrylate or methacrylate residues when subjected to radiation. It is preferred, however, that the alcohol residues are saturated.

Highly suitable mono alcohol residues in the composition of the invention include those of a saturate hydrocarbon, such as saturated aliphatic alkyl or hydrogenated rosin or a derivative thereof.

Favoured primary mono alcohol residues of saturated aliphatic alkyl includes those of a lower saturated alkyl which contain 1 to 5 carbon atoms. Apt primary mono alcohols of this type include those of ethanol or n-propanol.

The lower alkyl primary mono alcohol residues can advantageously contain a polar group such as a carboxyl group or a tertiary amine group which does not react or has a relatively low rate of reaction with an isocyanate. Apt primary mono alcohol residues of this type are those of N, N-diethylethanolamine. The presence of a polar group in the cured composition of the invention can provide a pressure sensitive adhesive with good cohesive properties.

Favoured primary mono alcohol residues of hydrogenated rosin or a derivative thereof include those of abietyl alcohols, a hydroabietyl alcohol or mixtures thereof. An apt primary mono alcohol resin of this type is known as Abitol available from Hercules Inc. Such residues being derived from a rosin can advantageously tackify a cured pressure sensitive adhesive composition of the invention. Apt compositions will suitably contain mixtures of, for example abitol and propanol, to give a final cured adhesive desired aggressiveness of adhesion.

Suitable residues of hydroxyalkyl acrylate or methacrylate include those in which the alkyl contains 2 to 4 carbon atoms.

Favoured residues of hydroxyalkyl acrylate or methacrylate in the composition of the invention are those of a hydroxyethylmethacrylate such as 2-hydroxy ethyl methacrylate and hydroxy ethyl acrylate.

Suitable polyurethanes for use in the composition can be derived from a polyester diol or preferably a polyether diol and a di-isocyanate.

Suitable polyether diols include polyoxyalkylene diols in which the alkylene contains 2 to 4 carbon atoms such as polyoxyethylene, polyoxypropylene and polyoxytetramethylene diols and mixtures thereof. Such polyether diols can suitably have an average molecular weight of 1000 to 8000 and preferably have a molecular weight of 1500 to 6000. A favoured polyether diol for forming the polyurethanes used in the invention is polyoxypropylene diol. An apt diol of this type is known as Ppg 2025, available from British Drug House, which has an average molecular weight of 2025. Another suitably hydrophilic group containing diol is a block copolymer of polypropylene glycol and ethylene oxide marketed as Dowfax 63N10 available from Dow Chemicals Inc.

Polyoxypropylene diol residues in the composition of the invention can render the radiation cured pressure sensitive adhesive formed therefrom moisture vapour transmitting.

In a preferred embodiment of the invention the polyurethane will contain oxyalkylene units derived from both polyoxyethylene diol and polyoxypropylene diol. Suitably the ratio of polyoxyethylene to polyoxypropylene residues can range from 20:80 to 80:20, for example 50:50. The residue species may be randomly arranged with respect to each other.

Diisocyanates used to form the polyurethane can suitably have an isocyanate functionality of 1.6–2.05 and can preferably have an isocyanate functionality of 2.0. Suitable diisocyanates include aliphatic (including alicyclic) and aromatic diisocyanates.

Favoured diisocyanates include toluene diisocyanate, 4,4$^1$-diphenylmethane diisocyanate and 4,4$^1$-dicyclo hexyl diisocyanate which is the preferred diisocyanate and which in an apt form is known as Desmodur W available from Bayer.

The polyurethane of the composition of the invention can be optionally derived from a chain extending agent. Suitable chain extending agents include diols such as ethane diol and butane diol, diamines for example ethylene diamine, and water.

The molar ratio of diol or diol and diamine residues to diisocyanate residues in the polyurethane can suitably be 0.6 to 0.8:1 and preferably 0.65 to 0.75:1 for example 0.7:1.

The curable composition may be prepared by reacting an isocyanate prepolymer, which itself can be the reaction product of polyfunctional isocyanate and the polyester or polyether diol, with the acrylate or methacrylate and the alcohol whereby the proportion of the acrylate or methacrylate is desirably such that it will react with at least from 15 to 25% of the free isocyanate groups in the prepolymer; the alcohol will react with the remainder of the isocyanate groups.

The molar ratio of hydroxylalkyl acrylate or methacrylate residues to alcohol residues in the polyurethane can suitably be 1:1 to 1:9 and can preferably be 1:1 to 1:5 for example 1:2.

The molar amount of hydroxyalkyl acrylate or methacrylate residues and alcohol residues in the polyurethane will normally be such as to render the capped polyurethane free of isocyanate groups.

The radiation curable composition of the invention can be prepared by first reacting appropriate amounts of the diisocyanate, the diol and optionally the chain extending agent components in a reaction vessel in the presence of suitable catalyst to form an isocyanate terminated prepolymer and then reacting the prepolymer with a mixture of the appropriate amounts of hydroxylalkyl acrylate or methacrylate and the alcohol to form the end capped polyurethane.

A suitable catalyst for the prepolymer reaction is dibutyl tin dilaurate, Catalyst T12 available from British Drug Houses is an example of such a catalyst. The prepolymer reaction can be carried at an elevated temperature, e.g. about 90° C. and a sufficient time, e.g. approximately one hour for the reaction to be completed. The reaction components are preferably preheated, e.g. to a temperature of approximately 60° C. before addition of the catalyst and are also protected from atmospheric moisture by a cover over the reaction vessel.

The amounts of diol and isocyanate can be chosen to a suitable NCO/OH ratio of from 1.2–4:1 whereby the prepolymer contains from 1.5 to 3.0% by weight of free isocyanate groups.

The end capping components can be added when the reaction mixture has cooled, e.g. to below 60° C. The reaction mixture can then be left preferably for greater than 3 days. An acrylic polymerisation inhibitor such as methoxyethyl hydroquimone (MEHQ) can be added to the reaction mixture with the end capping components to inhibit premature polymerisation.

The radiation curable composition of the invention can be cured by radiation to form a pressure sensitive adhesive.

Thus in another aspect the invention provides a pressure sensitive adhesive which comprises a radiation cured composition of the invention.

The curable compositions of the invention are normally viscous liquids which are capable of being coated as a layer onto a substrate at a temperature of 10° C. to 100° C., for example 60° C.

Pressure sensitive adhesive of the invention can be formed by coating a layer of the curable composition on a suitable substrate and exposing the layer to radiation such as ultra violet light or electron beam radiation. When the radiation is ultra violet light radiation, typically between 219 and 425 nm, the curable composition will also comprise a photoinitiator such as benzildimethyl ketal (typically about 1% by weight). Alternatively the composition may be thermally cured.

Electron beam radiation of the curable composition can be carried out by passing the composition as a layer on a substrate under the electron beam set to give a dose of 2 to 6 MRad and preferably a dose of 3 to 5 MRad for example 4 MRad. During radiation the composition is inhibited from contact by oxygen molecules by using an inert gas for example nitrogen atmosphere or by protecting the surface of the composition with a layer of barrier material. It has been fond that electron beam curing of curable compositions of the invention is sufficiently rapid to allow a pressure sensitive adhesive layer to be formed at speeds in the region of 100 meters/min.

A suitable electron beam machine for radiation curing the composition of the invention is known as an Electrocurtain machine M0175 available from Energy Sciences International.

When the compositions of the invention are thermally cured, an initiator such as AZO(bis-isobutyro nitrile) is typically included within the formulation.

The pressure sensitive adhesive layer formed by radiation of the curable composition will normally be on a substrate. The substrate can conveniently be a release sheet such as a silicone release coated paper or film which will allow transfer of the adhesive layer to another layer.

Adhesive products of the invention can be therefore formed by laminating the backing layer to the adhesive layer on the release sheet and then if necessary removing the release sheet. Alternatively the substrate can be the backing layer in which case the cured pressure adhesive can be formed directly on the backing layer.

Advantageously the pressure sensitive adhesive layer can be formed between two layers for example a backing layer and a release sheet. The use of two layers which are substantial barriers to oxygen, advantageously avoids the need to provide an oxygen free atmosphere for the curable composition during electron beam radiation.

Adhesive products such as dressings can then be formed from the adhesive coated substrate layer by conventional methods.

The polyurethane polymer so formed is a crosslinked polymer which is capable of absorbing from up to 50%, typically from 3 to 30%, by weight of water depending upon the reactants employed.

The water absorption of the adhesive can be obtained by taking a known weight of the dry adhesive (D) and immersing in water for 24 hours. The hydrated polymer is removed from the water, surface water is removed by lightly blotting with absorbent paper and then the weight of the hydrated adhesive (W) taken. The water absorption of the adhesive (% by weight) can then be calculated as $(W-D)\times 100/W$.

When formed into pressure sensitive adhesives, the cured composition of the invention may be characterised in having good adhesion values, both when the dry and after immersion in water up to 24 hours. The adhesives of the invention are thus water tolerant if when containing hydrophilic residues.

The pressure sensitive adhesive can form part of an adhesive product.

Thus in a further aspect the invention provides an adhesive product which comprises a pressure sensitive adhesive of the invention.

When coated onto a suitable substrate to form an adhesive product, the adhesive is aptly in the form of a continuous film. However, the adhesive layer or film may contain bubbles and may have the appearance of a foam because of such bubbles. Such bubbles do not adversly affect the adhesion or moisture vapour transmission characteristics of the adhesives or products made therefrom.

Desirably the adhesive product of the invention has a moisture vapour transmission rate of at least $300/m^2/24$ hours and suitably a moisture vapour transmission rate (MVTR) of at least $500 \ g/m^2/24$ hours at 37° C. at a relative humidity difference of 100% to 10%. Preferred products will have moisture vapour transmission rates in excess of about $1000 \ g/m^2$ when in contact with moisture vapour. The MVTR when measured in contact with moisture vapour is referred to us the 'upright' MVTR.

An adhesive product of the invention will normally comprise a layer of pressure sensitive adhesive of the invention on a backing layer. It is therefore desirable that both adhesive and backing layers of an adhesive product of the invention are moisture vapour transmitting.

Suitable moisture vapour transmitting adhesive layers include either a discontinuous layer of a pressure sensitive adhesive of the invention or a continuous layer of a pressure sensitive adhesive of the invention. Favoured moisture vapour transmitting continuous layers of pressure sensitive adhesive for use on adhesive products of the invention comprise polyurethanes containing either polyoxypropylene diol residues or mixtures of polyoxypropylene and polyoxyethylene diol residues.

The weight per unit area of the adhesive layer of a adhesive product of the invention can suitably be 10 to $300 \ g/m^2$, more suitably 10 to $200 \ g/m^2$ and can preferably be 20 to $80/m^2$.

Suitable moisture vapour transmitting backing layer for use in the adhesive product can include both discontinuous and continuous backing layers.

Suitable discontinuous backing layers include any of the discontinuous backing layers used in conventional medical and surgical products such as woven, knitted, mon-woven fabric, porous including microporous and apertured film backing layers.

Suitable moisture vapour transmitting continuous materials for backing layers include films of thermoplastic polyurethane, hydrophilic polyurethane and blends of polyurethane with an incompatible polymer. Other materials useful for backing layers are films derived from polyether polyamides or polyether polyesters.

Suitable films of thermoplastic polyurethane include those of thermoplastic polyether or polyester polyurethane for example those of Estane polyurethanes available from B.F. Goodrich.

Such films can suitably have a thickness of 15 to 75 $\mu m$ and can preferably have a thickness of 20 to 40 $\mu m$. An apt film for use in the invention comprises a thermoplastic polyether polyurethane known as Estane 5714 and ha a thickness of 25 $\mu m$ to 30 $\mu m$.

Suitable hydrophilic polyurethane films for use as a backing layer in an adhesive product of the invention are disclosed in European Patent No. 0091800.

Suitable films which comprise a blend of polyurethane and incompatible polymer for use as a backing layer in an adhesive product of the invention are disclosed in European Patent No 0046071.

Suitable polyether polyamide thermoplastic elastomers for use as backing layers will normally contain polyoxyalkylene blocks of molecular weight 200 to 6000 and will normally contain polyamide blocks of molecular weight 300 to 15000. Most suitably the polyether polyamide will be a linear copolymer with the polyalkylene blocks alternating with the polyamide blocks and interconnected by ester groups. The polyoxyalkylene blocks will usually be polyoxyethylene, polyoxypropylene or ply(tetramethyleneglycol) blocks or mixtures thereof.

The polyamide blocks may be products of the polymerisation of cycloalkyl lactams having 6 to 12 carbon atoms. Thy polyamides are preferably derived from the nylons 6, 6-6, 6-9, 6-10, 6-12, 9-6, 11 and 12. Polyether polyamide thermoplastic elastomers of this type are described in British Patent No. 1,473,992, French Patent Nos. 1,444,437 and 2,178,205 and U.S. Pat. No. 3,839,243.

Alternatively the polyamide blocks may be formed by reacting an aryl di-isocyanate with a carboxylic acid terminated polyether ester prepolymer Polyether polyamides of this type are disclose in U.S. Pat. No. 4,129,715.

Polyether polyamide thermoplastic elastomers may be obtained via ATO Chemie SA., La Defense 5, Cedex 24, Paris France and ATO Chemie (UK) Ltd., Colthrop Lane, Thatcham, Newbury, Berks. RG13 4NR, U.K. Alternatively they may be prepared by following the procedures of the aforementioned patents.

Favoured polyether polyamide thermoplastic elastomers for use in this invention include the PEBAX materials form ATO Chemie, for example Grades 4033SNOO, 2533SNOO and 5533SNOO. A favoured polyether polyamide thermoplastic elastomer is PEBAX 2533RNOO. Another favoured polyether polyamide thermoplastic elastomer is Estamid 90A obtainable from the Upjohn Company.

The polyether polyamide thermoplastic elastomer will normally contain polyether blocks containing 3 to 30 ether oxygen atoms linked to polyamide blocks by amide links. Polyether polyamide thermoplastic elastomers can be formed by reacting polyether diamine with a dicarboxylic acid for example a dimerised fatty and optionally in the present of nylon monomer such as caprolactam, laurolactam and H-aminoundecanoic acid.

The structure and preparation of polyether polyamide thermoplastic elastomers is described in British Patent No. 2044785A.

A favoured polyether polyamide thermoplastic elastomer is known as Grilon ELY1256 available from Grilon (UK) Limited.

Suitable polyether polyester thermoplastic elastomers for use as backing layers will normally contain polyoxyalkylene blocks of molecular weight from 350 to 6000. Most suitably the polyether polyester thermoplastic elastomer will contain long chain polyether ester units derived from a high molecular weight polyether glycol and an aromatic dicarboxylic acid linked to short chain ester units derived from an aliphatic glycol and an aromatic dicaboxylic acid.

Favoured polyether polyester thermoplastic elastomers contain polyoxytetramethylene) glycol terephthalate blocks.

The structure and preparation of suitable polyether polyester thermoplastic elastomers are described in British Patent No. 1,404,925, Belgian Patent No. 777023, U.S. Pat. No. 3,023,192 and in the Encyclopaedia of Polymer Science and Technology Supplement Volume 2, pages 485 to 510.

Suitable polyether polyester thermoplastic elastomers for use in the invention include Hytrel elastomers available from Dupont. Favoured Hytrel polyester elastomers are grades 4056, 5526, 6346 and 7246.

The thermoplastic elastomer can contain additives such as fillers and antioxidants.

The adhesive product of the invention can favourably be a surgical or medical adhesive dressing such as a first aid dressing, a wound dressing, an ulcer dressing or an adhesive drape.

In a further aspect, the present invention provides adhesive products comprising adhesives in accordance with the invention.

The adhesives of the present invention are suitable for use in a number of applications. These applications include use as the adhesive when coated on a substrate for bandages, absorbent dressings, wound dressings, burns dressings, incise drapes, first aid dressings, intravenous catheter dressings, ulcer dressings, ostomy devices, condom attachment in urinary incontinence devices, transdermal drug delivery devices, electroconductive gels, adhesive tapes (surgical tapes, wound closure tapes and the like), sanitary protection devices such as napkins, diapers, incontinence pads and protection pads against physical trauma or vibrations. However the main use is envisages to be in dressings and drapes of the types described above when the adhesive is in contact with the skin.

The adhesives of the invention may be employed in the manufacture of bacteria proof wound dressings such as those which comprise a backing layer which has upon substantially the whole of one surface thereof a layer of pressure sensitive adhesive in accordance with the invention. Such dressings will typically have a moisture vapour transmission rate of greater than 7000 gm$^{-2}$24h$^{-1}$ at 37° C. when the adhesive is in contact with water.

Suitably the adhesive layer may be microscopically continuous over the whole of the surface of the backing layer.

Many medicinal agents may be incorporated into the adhesives of the present invention. By medicinal agents it is meant pharmacologically active agents and agents including topical anaesthetics such as xylocaine, bacteriostatic agents such as silver nitrate; antibacterial agents of which preferred agents are silver sulphadiazine, chlorhexidine salts, PVP-I, and biguanides, antibiotics, topical steroids, enzymes, tissue stimulants, coagulants and anticoagulants and antifungal agents Other agents such as emollients may be added after the reaction step.

Advantageously water soluble medicaments such as chlorhexidine and its salts may be dissolved in the prepolymer. It is found that chlorhexidine is unaffected during the process and the resulting adhesive provides effective release of chlorhexidine when placed onto the skin.

A suitable method of determining the upright moisture vapour transmission rate of the dressing of this invention is as follows. Discs of material under test are clamped over Payne Permeability Cups (flanged metal cups) using sealing rings and screw clamps. The exposed surface area of the test sample may be conveniently 10 cm$^2$. Each cup contains approximately 10 ml of distilled water. After weighing the cups are placed in a fan assisted electric oven maintained at 37°±1° C. The relative humidity within the oven is maintained at 10% by placing 1 Kg of anhydrous 3-8 mesh calcium chloride on the floor of the oven. The cups are removed after 24 hours, allowed to cool for 20 minutes and reweighed. The MVTR of the test material is calculated from the weight loss expressed in units of grams of weight per square meter per 24 hours.

A suitable method of determining the inverted moisture vapour transmission rate of the dressing of this invention is as follows. The method described above is employed except that the Payne Cups are inverted in the oven so that the water within the cups is in contact with the test material and in this case with the adhesive.

The present invention further provides a method of treating a skin lesion such as a wound or intravenous (IV) injection site which comprises covering the lesion with a dressing coated with a cured composition in accordance with the invention.

The invention will now be illustrated by reference to the following examples.

EXAMPLE 1

Preparation of a Radiation Curable Composition of the Invention

In the preparation an isocyanate terminated prepolymer was initially formed by mixing Ppg 2025 (1 mole), 1,2-ethane diol (0.4 mole) and Desmodur W (2.03 mole), in a 500 ml jar, heating the mixture to 60° C., adding catalyst T12 (0.4 g) with stirring until bubbling ceased covering the jar with polytetrafluoroethylene film to exclude moisture and then heating the mixture to 90° C. for 1 hour in an oven to polymerise the reactants.

The radiation curable compositions was formed from the prepolymer by allowing the jar and the mixture to cool to approximately 60° C., adding to the mixture hydroxyethylmethacrylate (0.3 mole) n-propanol (0.9 mole) and MEHQ (500 ppm) and then allowing the mixture to stand for 3 days before it was used. The radiation curable composition so formed was a viscous colourless liquid which had a viscosity of approximate 20,000 p at 30° C.

EXAMPLE 2

A radiation curable composition of the invention was formed in the same manner as Example 1 except that N,N-diethylethanolamine (0.8 mole) instead of n-propanol and 0.4 mole instead of 0.3 mole of hydroxyethylmethacrylate were used.

The radiation curable composition of this example was a viscous slightly yellow liquid of similar viscosity to that of Example 1.

EXAMPLE 3

A radiation curable composition was prepared in the same manner as Example 2 except that Abitol (0.8 mole) was used instead of N,N-diethylethanolamine.

The radiation curable composition of this example was a viscous colourless liquid with a similar viscosity to that of Example 1.

EXAMPLE 4

Preparation of a Cured Pressure Sensitive Adhesive and Adhesive Coated Product

The radiation curable composition prepared in Example 1 was heated in a container over a water bath to 70° C. to reduce its viscosity to approximately 120,000 cp. The composition was then coated onto a silicone release coated paper using a hand coating device (gap 0.002") to give a coating with a weight per unit area of 40±10 g/m². Samples of the coated paper (6"×4") were then secured to a block and passed under an electron beam in an inert nitrogen atmosphere (<200 ppm $O_2$) by means of a conveyor (speed 30 m per minute) to radiation cure the composition and for a cured pressure sensitive adhesive of the invention.

The beam characteristics used were
Cathode Power—350 watts
Cathode Voltage—165 kV The beam current was adjusted to give a dose of 4 MRads. The electron beam machine used is known as Electrocurtain machine MO175 available from Energy Sciences International.

The pressure sensitive adhesive was transferred onto an Estane 5714 film (30 g/m²) by laminating the film to the adhesive on the paper to form an adhesive coated product of the invention.

The adhesive coated products was found to have a good adhesion to skin.

EXAMPLES 5 AND 6

Cured pressure sensitive adhesives and adhesive coated products of Examples 5 and 6 were prepared in the same manner as Example 4 using the radiation curable compositions of Examples 2 and 3 respectively.

The adhesive coated products of these examples were both found to have good adhesion to skin.

EXAMPLE 7

A cured pressure sensitive adhesive was formed on a silicone release coated paper in the same manner as Example 4 to give a weight per unit area of 70 g/m². The pressure sensitive adhesive was transferred on to a polyurethane-incompatible polymer blend film in the same manner as Example 4 to form an adhesive coated product of the invention.

The blend film used in this example had a weight per unit area of 74 g/m², comprises 60 parts by weight of a thermoplastic polyurethane (Estane 580201) and 40 parts by weight of a high impact polystyrene (Styron 485) and was made according to the method given in European Patent No. 0046071.

The adhesive coated product was found to have good adhesion to skin. The product had a moisture vapour transmission rate of 600 g/m²/24h at 37° C. at a relative humidity difference of 100% to 10%.

EXAMPLE 8

An isocyanate rich prepolymer was prepared by charging 136.6 g (1 mole) of Dowfax 63N10 (polyoxypropylene diol) and 1.64 g (0.4 mole) of ethane diol to a 500 ml glass jar and adding 35.85 g of Desmodur W and 0.2% by wt $T_{12}$ catalyst. The mixture was stirred, the jar covered with PTFE and heated in a fan assisted oven for 1 hour at 90° C.

The thus formed prepolymer was then cooled to 60° C. and 2.58 g (0.3 mole) of hydroxyethyl methacrylate, 22.64 g (0.9 mole) of Abitol and 0.049 g of MEHQ were added and mixed in after which the mixture was heated at 60° C. for a further hour and then allowed to cool.

EXAMPLE 9

The procedure of Example 8 was followed except that the hydroxyethylmethacrylate was replaced by 2.3 g (0.3 mole) of hydroxyethylacrylate.

EXAMPLES 10-12

The procedure of Example 8 was repeated except that the polyoxyalkylene diol component was derived from various mixtures of polyoxypropylene glycol (Ppg 2025) and polyoxyethylene glycol (PEG 1500).

The reactants employed were

|  | Example 10 | Example 11 | Example 12 |
|---|---|---|---|
| PPG 2025 (g) | 114.7 | 101.9 | 63.7 |
| PEG 1500 (g) | 9.84 | 19.67 | 49.18 |
| Mole Ratio PPG/PEG | 9:1 | 4:1 | 1:1 |
| Ethenediol (g) | 1.64 | 1.64 | 1.64 |
| Desmodur W (g) | 35.91 | 36.02 | 38.42 |
| $T_{12}$ | 0.4 | 0.4 | 0.4 |
| HEMA | 2.58 | 2.58 | 2.58 |
| Abitol | 22.64 | 22.64 | 25.8 |
| MEHQ | 0.04 | 0.04 | 0.04 |

EXAMPLES 13 AND 14

The procedure of Example 8 was repeated using the isocyanate MDI instead of Desmodur W and Ppg 2025 instead of Dowfax. The formulations were as follows.

|  | Ex 13 | Ex 14 |
|---|---|---|
| PPg 2025 (g) | 127.4 | 127.4 |
| HEMA (g) | 2.58 | 2.24 |
| Abitol (g) | 22.64 | 19.17 |
| Ethanediol (g) | 1.64 | — |
| MDI (g) | 34.12 | 25.8 |
| $T_{12}$ (g) | 0.4 | 0.35 |
| MEHQ (g) | 0.04 | 0.04 |

EXAMPLE 15

The curable compositions of Examples 8 to 14 were formed into adhesives by taking 10 g samples, warmed to 50° C. and mixing with 1% w/w of Irgacure 651 photoinitiator. The mixture was sandwiched between two polyethylene p-terephthalate (Melinex) films and compressed to a thickness of about 1 mm and placed beneath a Henovia UV lamp for five minutes.

Samples of the cured adhesive slabs were tested for hydration by soaking the slab in water overnight, having been weighed dry and re-weighing when hydrated. The water content is derived from the equation.

$$\frac{\text{Wet Mass} - \text{Dry Mass}}{\text{Wet Mass}} \times 100\%$$

The water contents, when hydrated, were as follows:

| Example | 8 | 9 | 10 | 11 | 12 | 13 | 14 |
|---------|---|---|----|----|----|----|----|
| Water % | 4 | 4 | 5  | 8  | 22 | <1 | 3  |

EXAMPLE 16

Dressings were prepared by coating a release coated paper to a thickness of 2 thou with the mixtures of Example 15 prepared from the compositions of Examples 9 and 14 covering the top surface with polyurethane film and curing the laminate for 10 minutes in a 48 watt UV light box.

The cured films were removed from the release paper and tested for moisture vapour transmission (upright and inverted) and peel strength after 24 hours immersion in water and 5 minutes or 24 hrs drying and after immersion in water for 24 hours followed by drying for five minutes.

The following results were obtained:

|  | Example 9 | Example 14 | PU Film Control |
|---|---|---|---|
| MVTR (Upright) ($gm^{-2}\ 24\ h^{-1}$) | 1075 | 855 | 1873 |
| MVTR (Inverted) ($gm^{-2}\ 24\ h^{-1}$) | 1248 | 913 | — |
| Peel Dry/5 mins ($Nm^{-1}$) | 246 | 165 | N/A |
| Peel Dry/24 hr ($Nm^{-1}$) | 252 | 134 | N/A |
| Peel Wet/Dry ($Nm^{-1}$) | 95 | 94 | N/A |

We claim:

1. A radiation or thermally curable composition for a pressure sensitive adhesive which comprises a polyurethane capped with residues of a hydroxyalkyl acrylate or methacrylate and non-polymerisable residues of a primary or secondary alcohol.

2. A composition according to claim 1 in which the polyurethane comprises residues of a polyether diol or a polyester diol.

3. A composition according to claim 1 wherein the alcohol is a mono-ol.

4. A composition according to claim 3 wherein the alcohol is an alkanol containing from 1 to 5 carbon atoms.

5. A composition according to claim 3 in which the alcohol is a hydrogenated rosin.

6. A composition according to claim 5 in which the alcohol is a hydroabietyl alcohol or a mixture of hydroabietyl alcohols.

7. A composition according to claim 1 wherein the acrylate or methacrylate is a $C_2$-$C_4$ alkyl acrylate or methacrylate.

8. A composition according to claim 2 wherein the diol is polyoxyalkylene diol.

9. A composition according to claim 8 wherein the polyoxyalkylene diol is polyoxypropylene diol or a mixture thereof with polyoxyethylene diol.

10. A pressure sensitive adhesive composition comprising a cured polyurethane capped with residues of a hydroxy alkyl acrylate or methacrylate and non-polymerisable residues of a primary or secondary alcohol.

11. A composition according to claim 10 which is radiation cured.

12. A composition according to claim 10 in which the polyurethane comprises residues of a polyether diol or a polyester diol.

13. A composition according to claim 11 wherein the alcohol is a mono-ol.

14. A composition according to claim 2 wherein the alcohol is an alkanol containing from 1 to 5 carbon atoms.

15. A composition according to claim 2 in which the alcohol is a hydrogenated rosin.

16. A composition according to claim 2 in which the alcohol is a hydroabietyl alcohol or a mixture of hydroabietyl alcohols.

17. A composition according to claim 11 wherein the acrylate or methacrylate is a $C_2$-$C_4$ alkyl acrylate or methacrylate.

18. A composition according to claim 2 wherein the diol is polyoxyalkylene diol.

19. A composition according to claim 2 wherein the polyoxyalkylene diol is polyoxypropylene diol or a mixture thereof with polyoxyethylene diol.

20. An adhesive dressing comprising a substrate having coated thereon a pressure sensitive adhesive comprising a cured polyurethane capped with residues of a hydroxyalkyl acrylate or methacrylate and non polymerisable residues of a primary or secondary alcohol.

21. A dressing according to claim 20 wherein the cured polyurethane is radiation cured.

22. A dressing according to claim 20 wherein the polyurethane contains residues of a polyether diol or a polyester diol.

23. A dressing according to claim 20 wherein the substrate is a polyurethane film a polyester polyamide film or a polyether polyamide film.

24. A dressing according to claim 20 which has a moisture vapour transmission rate of at least 1000 gm $m^{-2}\ 24\ hr^{-1}$ at 37° C. and a relative humidity difference of 100% to 10% when in contact with moisture vapour.

25. A dressing according to claim 20 in the form of a surgical incise drape.

26. A dressing according to claim 20 in the form of a skin lesion covering dressing.

27. A dressing according to claim 20 which contain a therapeutically effective amount of a medicament.

* * * * *